US006225533B1

(12) United States Patent
DeBonte et al.

(10) Patent No.: US 6,225,533 B1
(45) Date of Patent: *May 1, 2001

(54) LOW LEVEL GLUCOSINOLATE BRASSICA

(75) Inventors: Lorin Roger DeBonte; Zhegong Fan, both of Fort Collins, CO (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/240,831

(22) Filed: Feb. 1, 1999

Related U.S. Application Data

(63) Continuation of application No. 08/507,394, filed as application No. PCT/US94/01869 on Feb. 22, 1994, now Pat. No. 5,866,762, which is a continuation of application No. 08/023,238, filed on Feb. 25, 1993, now abandoned.

(51) Int. Cl.[7] .............................. A01H 5/00; A01H 5/10; A01H 1/06; C12N 15/01; C12P 7/64
(52) U.S. Cl. ......................... 800/306; 800/264; 800/270; 800/276
(58) Field of Search ................................. 800/264, 270, 800/276, 306

(56) References Cited

U.S. PATENT DOCUMENTS 5,077,071    12/1991    Strop .

FOREIGN PATENT DOCUMENTS

| 0 033 753 | 1/1984 | (EP) . |
| 0 289 183 | 2/1988 | (EP) . |
| 0 323 753 | 12/1989 | (EP) . |
| WO 92/03919 | 3/1992 | (WO) . |
| WO 94/19929 | 9/1994 | (WO) . |

OTHER PUBLICATIONS

1989–90 National Winter Rapeseed Variety Trial Miscellaneous Series Buttetin 140, published by the University of Idaho, pp. 1–56.

Auld et al., Registration of Cathy Rapeseed, Crop Science, 31:1710–1713 (1991).

Bell et al., Nutritional Evaluation of Very Low Glucosinolate Canola Meal, Can. J. Anim. Sci., 71:497–506 (1991).

Calhoun, W. et al., Registration of Indore Rapeseed, Crop Science 23:184–185 (1983).

Choesin et al., Allyl Isothiocyanate Release and the Allelopathic Potential of *Brassica Napus* (Brassicaceae)1, Am. J. Bot. 78(8):1083–1090 (1991).

Daun et al., Glucosinolates in Seeds and Residues, Analysis of Oilseeds, Fats and Fatty Foods, Rossell & Pritchard (Eds.), Elsevier Applied Science, New York, NY, pp. 184–225 (1991).

Downey et al., Principals of Cultivar Development, vol. 2 Crop Species, Macmillan Publishing Co., New York, Fehr. W.R. Ed., Ch. 12, pp. 437–486.

F. Shahidi, J. of Food Quality, Individual Glucosinoltes in Six Canola Varieties, 11:421–431, 1989.

Haughn et al., Biochemical Genetics of Plant Secondary Metabolites in *Arabidopsis thaliana*[1], Plant Physiol., 97:217–226 (1991).

Ibrahim et al., Engineering Altered Glucosinolate Biosynthesis By Two Alternative Strategies, Genetic Engineering of Plant Secondary Metabolism, 28:125–152 (1994).

Koritsas et al., Glucosinolate Responses of Oilseed Rape, Mustard and Kale to Mechanical Wounding and Infestation by Cabbage Stem Flea Beetle (*Psylliodes chrysocephala*), Ann. Appl. Biol., vol. 118, pp. 209–221 (1991).

Kraling et al., Variation of Seed Glucosinolates in Lines of *Brassica napus*, Plant Breeding, 105:33–39, 1990.

Lichter et al., Glucosinolates Determined by HPLC in the Seeds of Microspore–Derived Homozygous Lines of Rapeseed (*Brassica napus* L.), Plant Breeding, 100:209–221, 1988.

Love et al., Development of Low Glucosinolate Mustard, Can. J. Plant Sci., 70:419–424, 1990.

Pleines, et al., Recurrent Selection for Modified Polyenoic Fatty Acid Composition in Rapeseed (*Brassica napus* L.), Proc. 7th Intl. Rapeseed Congress, p. 23 (1987).

Rakow et al., Opportunities and Problems in Modification of Levels of Rapeseed $C_{18}$ Unsaturated Fatty Acids[1], J. Am. Oil Chem. Soc., 50:400–403 (1973).

Ram et al., Biotechnology for Brassica and Hellanthus Improvement, Proc. World Conf. Biotechnol. Fat Oils Ind., AOCS: Champaign, IL, pp. 65–71.

Shpota, V.I., Rape and Mustard Breeding for Oil Quality, Proc. 7th Intl. Rapeseed Congress, pp. 560–565 (1987).

*Primary Examiner*—David T. Fox
(74) *Attorney, Agent, or Firm*—Fish & Richardson, P.C.

(57) ABSTRACT

Brassica seeds having a maximum of glucosinolate content of 3.4 μmoles per gram of seed, plant lines and progeny thereof which produces such seeds, and meal derived from such seeds are disclosed.

3 Claims, 2 Drawing Sheets

LOW LEVEL GLUCOSINOLATE BRASSICA

This application is a continuation of U.S. application Ser. No. 08/507,394 filed Nov. 1, 1995 now U.S. Pat. No. 5,866,762; which is a national stage application of PCT/US94/01869, filed Feb. 22, 1994, which is a continuation of U.S. application Ser. No. 08/023,238, filed Feb. 25, 1993 (abandoned).

FIELD OF THE INVENTION

The present invention relates to Brassica seeds, meal, plant lines and progeny thereof having a reduced level of glucosinolates.

Canola meal is widely employed as a protein supplement in animal feed. The feeding value of canola meal is reduced due to the anti-nutritive effects of the breakdown products of the glucosinolates, which reduce feed intake and growth in non-ruminant animals. Glucosinolates in the seed are broken down during the extraction process by the enzyme myrosinase to form isothiocyanates and nitriles. These breakdown products may also inhibit thyroid function, leading to goiter.

The feed value of canola meal can be improved by reducing or eliminating glucosinolates from canola seeds. Typical glucosinolate levels in canola meal and seed are disclosed in the following references: 1) Shahidi et al. Journal of Food Quality, 11, 421–431 (1989), and 2) Lichter et al., Plant Breeding 100, 209–221 (1988) and 3) Kraling et al., Plant Breeding, 105, 33–39 (1990). The typical range for the glucosinolates content of conventional *B. napus* double low canola varieties in $\mu$mol/g of seed at 40% oil content and 8.5% moisture is as follows:

| | |
|---|---|
| 2-hydroxy 3-butenyl glucosinolate | 2.40–7.32 |
| allyl glucosinolate | 0–1.16 |
| 2-hydroxy 4-pentenyl glucosinolate | 0–0.43 |
| 3-butenyl glucosinolate | 1.65–3.44 |
| 4-hydroxy 3-indolymethyl glucosinolate | 2.60–4.40 |
| 4-pentenyl glucosinolate | 0–1.14 |
| 3-indolylmethyl glucosinolate | 0–4.18 |
| Total glucosinolates | 12.06–18.23 |

By creating specific mutations in the glucosinolate biosynthetic pathway, mutations at various steps in the pathway may be combined to reduce the total glucosinolate levels in finished varieties. A. *B. rapa* line (BC86-18) with low glucosinolates levels has been identified via selection by Bell et al., Can: J. Animal Sci., 71, 497–506 (1991). However, the variability in glucosinolates content of *B. napus* germplasm is limited. The present invention provides *B. napus* lines, seeds, and meal having a reduced level of glucosinolates.

SUMMARY OF THE INVENTION

The present invention comprises a seed comprising a *Brassica napus* canola variety having a maximum content of glucosinolates of about 3.4 $\mu$mol/g seed and belonging to a line in which said glucosinolate content has been stabilized for both the generation to which the seed belongs and its parent generation and progeny thereof.

The present invention further comprises a plant line comprising a *Brassica napus* canola variety which produces seeds having a maximum content of glucosinolates of about 3.4 $\mu$mol/g seed and in which said glucosinolate content is stabilized for both the generation to which the seed belongs and its parent generation.

The present invention further comprises a canola meal derived from the above-described seeds. This canola meal has a maximum content of glucosinolates of 5.7 $\mu$mol/g of oil free meal.

DETAILED DESCRIPTION OF THE INVENTION

Figure 1:
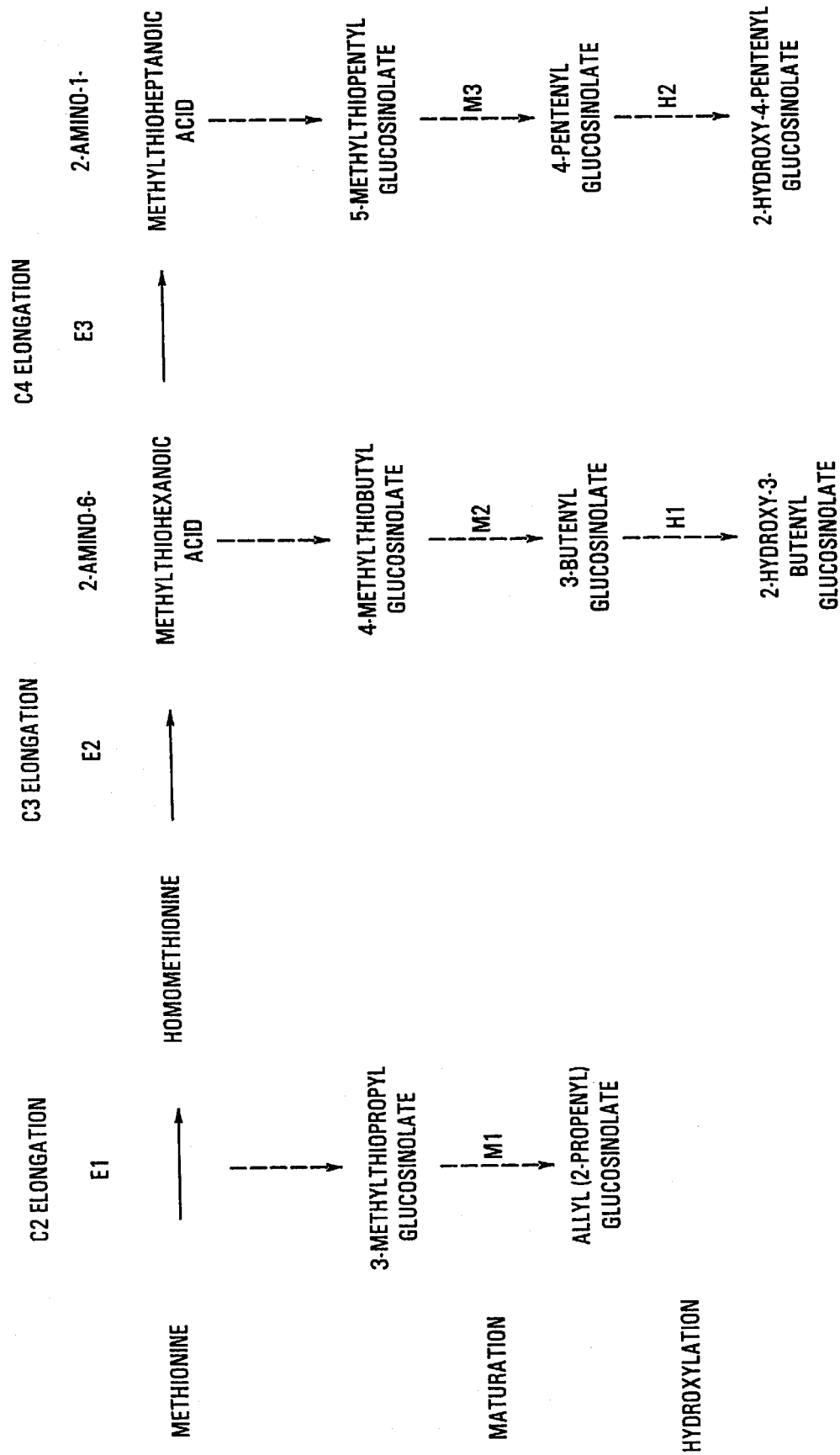
FIG. 1 shows the biosynthetic pathway of Major Aliphatic Glucosinolates in Brassica.

The present invention provides seeds, meal and plant lines having a reduced level of glucosinolates generated by creating specific mutations in the glucosinolate biosynthetic pathway. FIG. 1 depicts the biosynthetic pathway of major aliphatic glucosinolates in Brassica. As used herein, a "line" is a group of plants that display little or no genetic variation between individuals for at least one trait. Such lines may be created by several generations of self-pollination and selection, or vegetative propagation from a single parent using tissue or cell culture techniques. As used herein, the term "variety" refers to a line which is used for commercial production.

As used herein, "mutation" refers to a detectable and heritable genetic change not caused by segregation or genetic recombination. "Mutant" refers to an individual, or lineage of individuals, possessing a genetic mutation. The term "Mutagenesis" refers to the use of a mutagenic agent to induce random genetic mutations within a population of individuals. The treated population, or a subsequent generation of that population, is then screened for usable trait(s) that result from the mutations. A "population" is any group of individuals that share a common gene pool. As used herein "$M_0$" is untreated seed. As used herein, "$M_1$" is the seed (and resulting plants) exposed to a mutagenic agent, while "$M_2$" is the progeny (seeds and plants) of self-polinated $M_1$ plants, "$M_3$" is the progeny of self-pollinated $M_2$ plants, and "$M_4$" is the progeny of self-pollinated $M_3$ plants "$M_5$" is the progeny of self-pollinated $M_4$ plants. "$M_6$", "$M_7$", etc. are each the progeny of self-pollinated plants of the previous generation.

The term "progeny" as used herein means the plants and seeds of all subsequent generations resulting from a particular designated generation.

The term "selfed" as used herein means self-pollinated.

"Stability" or "stable" as used herein means that with respect to a given component, the component is maintained from generation to generation for at least two generations and preferably at least three generations at substantially the same level, e.g., preferably ±15%, more preferably ±10%, most preferably ±5%. The method of invention is capable of creating lines with improved glucosinolate compositions stable up to ±5% from generation to generation. The above stability may be affected by temperature, location, soil fertility, stress and time of planting. Thus, comparison of glucosinolate profiles should be made from seeds produced under similar growing conditions. Stability may be measured based on knowledge of prior generation.

Intensive breeding has produced Brassica plants whose seed oil contains less than 2% erucic acid. The same varieties have also been bred so that the defatted meal contains less than 30 $\mu$mol glucosinolates/gram. "Canola seed" is referred to herein as the seed of the genus Brassica which shall contain less than 30 μmoles of total glucosinolates per gram of whole seed at a moisture content of 8.5%; and the oil component of such seed shall contain less than 2% of all fatty acids as erucic acid.

The term "canola meal" is used herein to describe a protein meal derived from seeds of the genus Brassica containing less than 30 μmoles of total glucosinolates per gram of defatted meal at a moisture content of 8.5%.

The term "canola oil" is used herein to describe an oil derived from the seed of the genus Brassica, with less than 2% of all fatty acids as erucic acid.

The glucosinolate contents for the present invention are reported as μmol/gm seed at 40% oil content and at a moisture content of 8.5%. To compare, the reported values to older references μmol/gm of seed can be converted to μmol/gm of oil free meal, at 8.5% moisture using the following conversion: (μmol/gm seed)/(1.0–0.4). A comparison of this conversion from μmol of glucosinolates/gm of seed to μmol of glucosinolates/gm of defatted meal at 8.5% moisture using field grown IMC 129 seed is presented in Table V in Example 1 hereinafter.

Figure 2:
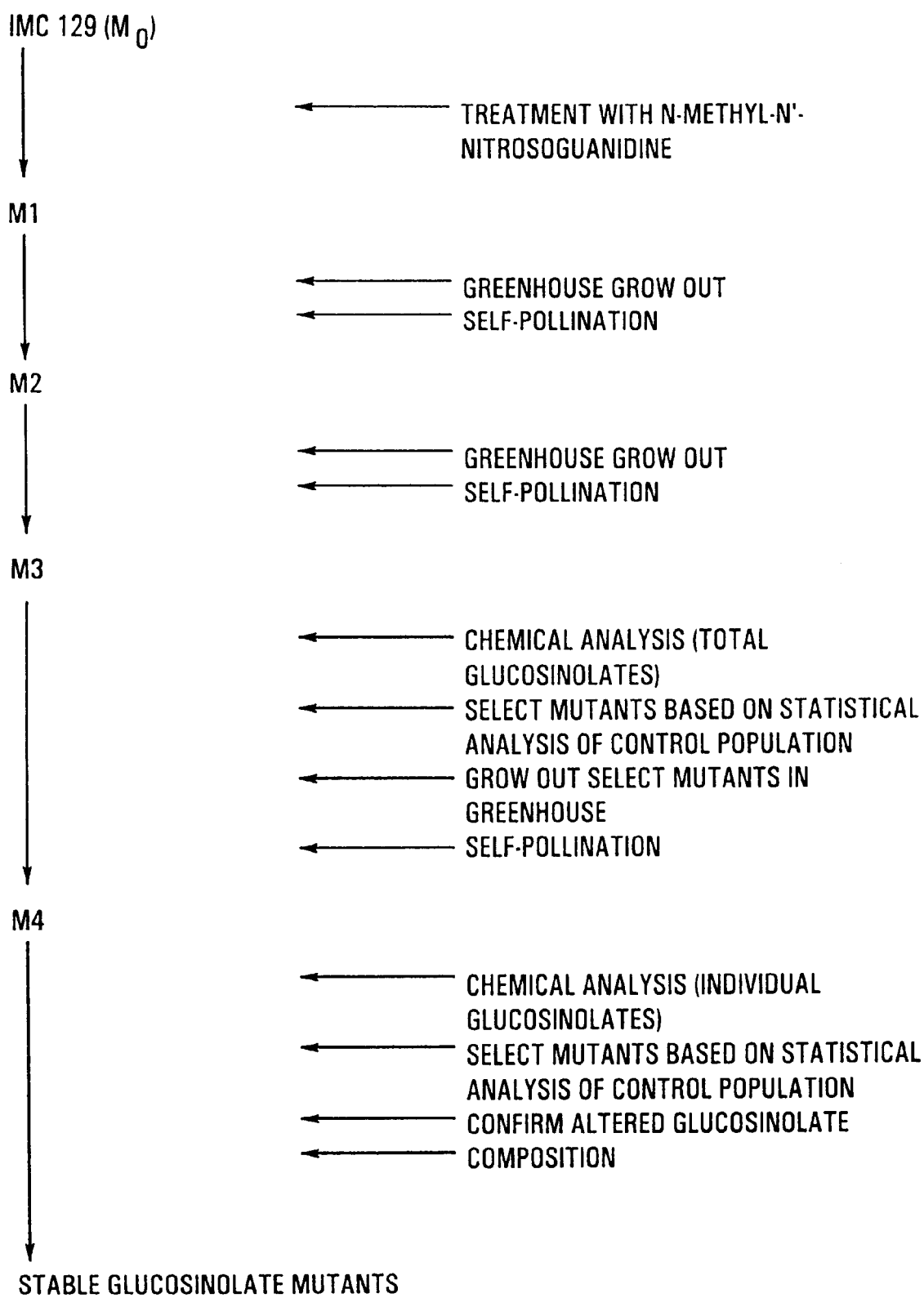
FIG. 2 shows the general experimental scheme for developing lines with stable lowered glucosinolate mutations.

The general experimental scheme for developing lines with stable lowered glucosinolate mutations is shown in FIG. 2 hereinafter.

IMC 129 seeds ($M_0$) were mutagenized with N-methyl-N'-nitro-N-nitrosoguanidine (MNNG). IMC 129 is a canola quality commercial Spring variety with high oleic acid grown by InterMountain Canola Inc. in the northwestern United States registered under U.S. Plant Variety Protection Certificate 9100151. The glucosinolate composition of field-grown IMC 129 has remained stable under commercial production. The glucosinolate composition as μmoles per gram of whole seed at a moisture content of 8.5% and 40% oil content is as follows: 8.77 of total glucosinolates, 3.97 of 2-hydroxy-3-butenyl glucosinolate, 0.38 of allyl glucosinolate, 0.35 of 2-hydroxy-4-pentyl glucosinolate, 1.84 of 3-butenyl glucosinolate, 1.66 of 4-hydroxy-3-indolyl methyl glucosinolate, 0.22 of 4-pentyl glucosinolate, and 0.32 of 3-indolylmethyl glucosinolate.

The disclosed method may be applied to all oilseed Brassica species, and to both Spring and Winter maturing types within each species. Physical mutagens, including but not limited to X-rays, UV rays, and other physical treatments which cause chromosome damage, and other chemical mutagens, including but not limited to ethidium bromide, nitrosoguanidine, diepoxybutane etc. may also be used to induce mutations. The mutagenesis treatment may also be applied to other stages of plant development, including but not limited to cell culture, embryos, microspores and shoot apices. Once the mutation has been identified it can be transferred into other B. napus varieties by cross-pollination. The present invention includes such cross-pollinated species.

The $M_1$ seeds derived from the mutagenesis treatment were planted in the greenhouse and $M_1$ plants were individually self-pollinated. $M_2$ seed was harvested and planted in the greenhouse, and individually self-pollinated to advance to the next generation. $M_3$ seeds were screened for total glucosinolate content using a TruBluGlu meter. This meter is available from Dr. R. J. W. Truscott at Systrix Pty. Ltd., University of Wollongong, P.O. Box 1144, Wollongong, N.S.W. 25000, Australia. The analytical procedure employed is detailed in Truscott et al. Proceedings of the Eighth International Rapeseed Congress 1991, McGregor, D., Ed., Vol. 5, pp. 1425–1427. Further details are provided in Example 1 herein after.

$M_4$ seeds were analyzed by high pressure liquid chromatography to determine specific alterations in the glucosinolate composition. Those lines which remained stable in glucosinolate content were regarded as stable mutations.

$M_4$ seeds were evaluated for mutations on the basis of a Z-distribution. An extremely stringent 1 in 10,000 rejection rate was employed to establish statistical thresholds to distinguish mutation events from existing variation. Mean and standard deviation values were determined from the non-mutagenized IMC 129 control population. The upper and lower statistical thresholds for each glucosinolate were determined from the mean value of the population±the standard deviation, multiplied by the Z-distribution. Based on a population size of 10,000, the confidence interval is 99.99%.

"Stable mutations" as used herein are defined as $M_3$ or more advanced lines which maintain a selected altered glucosinolate profile for a minimum of three generations, and exceeding established statistical thresholds for a minimum of two generations, as determined by liquid chromatographic analysis of a minimum of 200 mg (approximately 50 seeds) of randomly selected seeds. Alternatively, stability may be measured in the same way by comparing to subsequent generations. In subsequent generations, stability is defined as having similar glucosinolate profiles in the seed as that of the prior or subsequent generation when grown under substantially similar conditions.

The seeds of several lines having lowered glucosinolate content have been deposited with the American Type Culture Collection and have the following accession numbers.

| Line | Accession No. |
| --- | --- |
| 3Q0211 | 75419 |
| 3Q1552 | 75420 |
| 3Q0811 | 75421 |
| 3Q1273 | 75422 |

Stable mutants having reduced levels of glucosinolates were obtained. Seeds and plant lines producing such seeds, having a maximum glucosinolate content of 3.4 μmoles per g seed were obtained. Generally, the total glucosinolate as μmol/g of seed ranged from 2.01 to 3.41. The maximum content and range for the individual glucosinolates is as follows as μmol/g seed at 8.5% moisture and 40% oil content:

| | μ moles/g seed | |
| --- | --- | --- |
| Glucosinolate | Range | Maximum |
| 2-Hydroxy-3-butenyl | 0.26–1.50 | 1.50 |
| 2-Hydroxy-4-pentenyl | 0.03–0.13 | 0.13 |
| 3-Butenyl | 0.15–1.10 | 1.10 |
| 4-Hydroxy-3-indolylmethyl | 0.67–1.85 | 1.85 |
| 4-Pentenyl | 0.01–0.06 | 0.06 |
| 3-Indolylmethyl | 0.06–0.15 | 0.15 |
| Total Glucosinolates | 2.01–3.41 | 3.41 |

The glucosinolate content of the canola meal derived from the seeds of these stable mutants was calculated as previously described from the seed glucosinolate content. The meal has a maximum total glucosinolate content of 5.7 μmol/g on an oil free basis at 8.5% moisture. Generally, the total glucosinolate content ranged from 3.4 to 5.7 μmol/g.

The individual glucosinolate levels are as follows in μmol/g of oil free meal at 8.5% moisture.

| Glucosinolate | μmoles/g meal |
|---|---|
| 2-Hydroxy-3-butenyl | 0.43–2.50 |
| 2-Hydroxy-4-pentenyl | 0.05–0.22 |
| 3-Butenyl | 0.25–1.83 |
| 4-Hydroxy-3-indolylmethyl | 1.12–1.75 |
| 4-Pentenyl | 0.02–0.10 |
| 3-Indolylmethyl | 0.10–0.25 |
| Total Glucosinolates | 3.35–5.68 |

While the invention is susceptible to various modifications and alternative forms, certain specific embodiments thereof are described in the general methods and examples set forth below. For example the invention may be applied to all Brassica species, including *B. rapa, B juncea,* and *B. hirta,* to produce substantially similar results. It should be understood, however, that these examples are not intended to limit the invention to the particular forms disclosed but, instead the invention is to cover all modifications, equivalents and alternatives falling within the scope of the invention. This includes the use of somaclonal variation; antisense expression; transposon mutagenesis; physical or chemical mutagenesis of plant parts; anther, microspore or ovary culture followed by chromosome doubling; or self- or cross-pollination to transmit the glucosinolate trait, alone in combination with other traits, to develop new Brassica lines.

EXAMPLE 1

IMC 129 seeds ($M_0$) were mutagenized with N-methyl-N'-nitro-N-nitrosoguanidine (MNNG). IMC 129 is a canola quality commercial spring variety with high oleic acid grown by InterMountain Canola Inc. in the northwestern United States. The glucosinolate composition of field-grown IMC 129 is a described above and has remained stable under commercial production.

Prior to mutagenesis, 45,000 seeds of IMC129 were preimbibed in 300 seed lots for two hours on wet filter paper saturated in 0.05 M Sorenson's buffer (pH 6.1). The preimbibed seeds were placed in 1.0 mM MNNG for three hours. Following mutagenesis, the seeds were rinsed three times in Sorenson's buffer. The $M_1$ seeds were sown in 4 inch pots containing Pro-Mix. Approximately 21% of the mutagenized seed survived. The plants were maintained at 25° C./15° C., 14/10 hour day/night conditions in the greenhouse. At flowering, each plant was individually self-pollinated.

The $M_2$ seed from individual plants were catalogued and stored. Approximately 9,500 individual $M_2$ lines were sown in the greenhouse in 4 inch pots containing Pro-Mix soil. The plants were maintained at 25° C./15° C., 14/10 hour day/night cycle in the greenhouse. At flowering, the terminal raceme was self-pollinated by bagging. At maturity, selfed $M_3$ seed was individually harvested from each plant and catalogued.

The $M_3$ seed was screened using the TruBluGlu meter available from Dr. R. J. W. Truscott at Systrix Pty, Ltd., University of Wollongong, P.O. Box 1144, Wollongong, N.S.W. 2500, Australia. The details of the method used are as follows:

Two hundred milligrams (200 mg) of whole seeds were placed in a 15 mL polypropylene centrifuge tube. The seeds were crushed with a glass rod manually. Then 1.0 mL of 50 mM glycine-sodium hydroxide buffer, pH 9.0, was added and mixed well by using the glass rod. The rod was rinsed with 4.0 mL of glycine-sodium hydroxide buffer and filled to the 5 mL mark on the tube. The sample was incubated at room temperature for 10 min. Then 1.0 mL of chloroform was added, the tube capped and shaken vigorously. 50 mL of 10% chlorohexidine/methanol solution was added and mixed well. 1.0 mL of 100 mM sodium citrate buffer, pH 5.0, was added and mixed. Approximately 250 mg of activated carbon was added, shaken vigorously, and centrifuged for 15 min. using a bench-top centrifuge at 2000 rpm. One Clinistix (NDC 0193-2844-50, Miles) was immersed into the clean supernatant for 5 sec., excess supernatant shaken off and set aside for exactly 2 min. The color change was read by a TruBluGlu meter. Triplicate determinations were made for each sample. The TruBluGlu meters were calibrated using water and 1 mM glucose solution before reading samples.

Selected $M_3$ lines with less than 3 μmol/g of seed of total glucosinolates were sown in the greenhouse in 4 inch pots containing ProMix soil. The plants were maintained at 25° C./15° C. under 14/10 hour day/night conditions in the greenhouse. At flowering, each plant was individually self-pollinated. At maturity, the $M_4$ seed was harvested from each plant and catalogued.

Bulk seed of selected $M_4$ lines was analyzed for glucosinolate composition via high pressure liquid chromatography. The method developed by Daun and McGregor (1991) was used with modification to analyze the seeds as follows:

Extraction of glucosinolates: Ground seed (200 mg) was weighed into a test tube. The tube containing ground seed was placed in a water bath at 95° C. and left for 15 min. One mL boiling water was added to the tube and mixed well with the ground seed. After 3 min. the tube was withdrawn and cooled for 30 min. One mL of 1 mM benzyl glucosinolate solution was added into the tube as the internal standard and then mixed by vortexing. 100 μl of lead acetate and barium acetate solution were added and then centrifuged at 500×g for 20 min. The supernatant was retained as the glucosinolate extract.

Preparation of desulfoglucosinolates: One mL of glucosinolates extract was transferred to a micro column containing DEAE-Sephadex A-25 ion exchange resin. The extract was run into the column and washed with 3 mL of 0.02M pyridine acetate solution. Purified sulfatase solution (0.5 mL) was added into the column. When the enzyme solution had completely entered the column, the flow was stopped, the column capped, and allowed to stand at room temperature overnight. The desulfoglucosinolates were eluted with 2 mL of water into vials for HPLC analysis.

Profile anaysis by HPLC: Fifty microliters (50 μl) of the desulfoglucosinolates preparation were injected into a high performance liquid chromatograph (Hewlett-Packard 1050) equipped with a C-18 column (Pierce, 220×4.6 mm). The run was carried out with a solvent gradient program of 1 min. at 100% water, linear gradient over 15 min. to 75% water and 25% acetonitrile, held for 5 min., linear gradient over 5 min. to 100% water, held for 5 min. The flow rate was 1.5 ml/min. and the column temperature was 30° C. A UV detector was used at 227 nm.

The means and standard deviations were calculated from an external control population of non-mutagenized IMC 129 grown next to the mutagenized lines. Statistical thresholds were established for the glucosinolates using the control populations. The lower thresholds were determined to be 3.6 standard deviations below the IMC 129 control means with a 99.99% confidence interval. The lower thresholds used in the greenhouse selection are listed in Table IV. Selected M4 lines with altered glucosinolate compositions were planted in the greenhouse to advance the next generation.

Table I summarizes the reduced level of glucosinolates for the mutant lines generated. Significant reductions in the levels of 2-hydroxy-3-butenyl glucosinolate, 3-butenyl glucosinolate, and 4-hydroxy-3-indolylmethyl glucosinolate contributed to the overall low levels of total glucosinolates.

Fifteen lines with low progoitrin (2-hydroxy-3-butenyl glucosinolate) of less than 1.5 µmol/g seed have been produced via mutagenesis (Table II). The range of progoitrin in the mutations is 0.26–0.97 µmol/gm of seed. These lines also exceed the lower statistical threshold for 3-butenyl glucosinolate. Five of the low progoitrin selection were also below the lower selection for 4-hydroxy-3-indolylmethyl glucosinolate.

Six additional lines with low 4-hydroxy-3-indolylmethyl glucosinolate of less than 1.05 µmol/g seed have been produced via mutagenesis (Table III). The individual mutants range from 0.75–0.84 µmol/g seed. All of these mutations are below the statistical threshold for low total glucosinolates.

Table I presents the resulting overall glucosinolate compositions for the mutant lines of the present invention. Table II presents the resulting glucosinolate compositions of mutants having low 2-hydroxy-3-butenyl glucosinolate for several indicated lines. Table III presents the glucosinolate compositions of selected mutants with low 4-hydroxy-3-indolylmethyl glucosinolate for the lines indicated. Table IV illustrates the statistical thresholds employed for selection of the low glucosinolate mutations. Table V presents glucosinolate values for the control IMC 129. All values represent µmoles glucosinolate per gram of seed at 8.5% moisture and 40% oil content or per gram of oil free meal at 8.5% moisture as indicated.

The following abbreviations are used in Tables I through V for the various glucosinolates:

| | |
|---|---|
| PROG (Progoitrin) | 2-Hydroxy-3-butenyl glucosinolate |
| ALLYL (Sinigrin) | Allyl glucosinolate |
| NAPOL (Napoleiferin) | 2-Hydroxy-4-pentenyl glucosinolate |
| GLUCO (Gluconapin) | 3-Butenyl glucosinolate |
| 4-OH (4-OH Glucobrassicin) | 4-Hydroxy-3-indolylmethyl glucosinolate |
| GLUCOBN (Glucobrassicanapin) | 4-Pentenyl glucosinolate |
| GLUCOBB (Glucobrassicin) | 3-Indolylmethyl glucosinolate |

TABLE I

Glucosinolate Compositions of All Mutant Lines
µmoles glucosinolate/g seed

| LINES | PROG | ALLYL | NAPOL | GLUCO | 4-OH | GLUCOBN | GLUCOBB | TOTAL |
|---|---|---|---|---|---|---|---|---|
| max. observed | 1.50 | — | 0.13 | 1.10 | 1.05 | 0.06 | 0.15 | 3.41 |
| min. observed | 0.26 | — | 0.03 | 0.15 | 0.67 | 0.01 | 0.06 | 2.01 |

TABLE II

Glucosinolate Compositions of Mutants with Low Progoitrin
µmoles glucosinolate/g seed

| LINES | PROG | ALLYL | NAPOL | GLUCO | 4-OH | GLUCOBN | GLUCOBB | TOTAL |
|---|---|---|---|---|---|---|---|---|
| 3Q1553 | 0.26 | tr | tr | 0.15 | 1.85 | 0.01 | 0.15 | 2.42 |
| 3Q0211 | 0.46 | tr | 0.06 | 1.10 | 0.92 | 0.02 | 0.09 | 2.64 |
| 3Q1552 | 0.47 | tr | 0.05 | 0.27 | 1.38 | 0.01 | 0.09 | 2.27 |
| 3Q1314 | 0.65 | tr | 0.05 | 0.40 | 1.37 | 0.02 | 0.08 | 2.57 |
| 3Q1479 | 0.65 | tr | 0.08 | 0.38 | 1.43 | 0.02 | 0.13 | 2.69 |
| 3Q0517 | 0.72 | tr | 0.06 | 0.46 | 0.67 | 0.02 | 0.08 | 2.01 |
| 3Q1362 | 0.79 | tr | 0.06 | 0.45 | 0.88 | 0.02 | 0.09 | 2.29 |
| 3Q0837 | 0.81 | tr | 0.05 | 0.38 | 1.33 | 0.03 | 0.10 | 2.69 |
| 3Q1050 | 0.85 | tr | 0.08 | 0.48 | 1.01 | 0.03 | 0.07 | 2.52 |
| 3Q1283 | 0.88 | tr | 0.06 | 0.41 | 0.92 | 0.03 | 0.11 | 2.40 |
| 3QA208 | 0.89 | tr | 0.08 | 0.54 | 1.06 | 0.03 | 0.09 | 2.69 |
| 3Q1387 | 0.91 | tr | 0.10 | 0.55 | 0.74 | 0.05 | 0.09 | 2.45 |
| 3Q0482 | 0.95 | tr | 0.09 | 0.52 | 1.17 | 0.04 | 0.12 | 2.89 |
| 3Q8930 | 0.96 | tr | 0.03 | 0.57 | 1.20 | 0.03 | 0.12 | 2.91 |
| 3Q9289 | 0.97 | tr | 0.09 | 0.52 | 1.34 | 0.03 | 0.09 | 3.05 |

TABLE III

Glucosinolate Compositions of Selected Mutants with Low 4-OH Glucobrassicin
μmoles glucosinolate/g seed

| LINES | PROG | ALLYL | NAPOL | GLUCO | 4-OH | GLUCOBN | GLUCOBB | TOTAL |
|---|---|---|---|---|---|---|---|---|
| 3Q1273 | 1.32 | tr | 0.09 | 0.72 | 0.75 | 0.03 | 0.09 | 2.99 |
| 3Q0811 | 1.03 | tr | 0.09 | 0.54 | 0.79 | 0.03 | 0.09 | 2.58 |
| 3Q1269 | 1.50 | tr | 0.11 | 0.86 | 0.80 | 0.04 | 0.09 | 3.40 |
| 3Q1372 | 1.36 | tr | 0.10 | 0.74 | 0.80 | 0.03 | 0.11 | 3.14 |
| 3Q1367 | 1.47 | tr | 0.13 | 0.86 | 0.81 | 0.06 | 0.06 | 3.41 |
| 3Q1350 | 1.32 | tr | 0.07 | 0.56 | 0.84 | 0.03 | 0.07 | 2.89 |

TABLE IV

Statistical Thresholds for Selecting Low Glucosinolates Mutations
μmoles glucosinolate/g seed

| LINES | PROG | ALLYL | NAPOL | GLUCO | 4-OH | GLUCOBN | GLUCOBB | TOTAL |
|---|---|---|---|---|---|---|---|---|
| Average | 2.71 | tr | 0.22 | 1.49 | 1.37 | 0.11 | 0.40 | 6.23 |
| Std. Dev. | 0.13 | tr | 0.01 | 0.06 | 0.09 | 0.01 | 0.02 | 0.24 |
| Lower Threshold | 2.24 | tr | 0.18 | 1.27 | 1.05 | 0.07 | 0.33 | 5.37 |

TABLE V

Control: IMC 129 Glucosinolate values
μmoles glucosinolate per g seed or per g meal

| LINES | PROG | ALLYL | NAPOL | GLUCO | 4-OH | GLUCOBN | GLUCOBB | TOTAL |
|---|---|---|---|---|---|---|---|---|
| Whole Seed | 3.97 | 0.38 | 0.35 | 1.84 | 1.66 | 0.22 | 0.32 | 8.77 |
| Oil Free Meal | 6.43 | 0.61 | 0.55 | 2.97 | 2.69 | 0.35 | 0.515 | 14.14 |

What is claimed is:

1. A seed of a *Brassica napus* plant line having a maximum total glucosinolate content of about 3.4 μmoles per g seed and a maximum 4-hydroxy-3-indolylmethyl glucosinolate content of about 1.9 μmoles per g seed, wherein said total glucosinolate content is obtained by genetic mutation.

2. Progeny of the seed of claim 1, said progeny having said maximum total glucosinolate content and said maximum 4-hydroxy-3-indolylmethyl glucosinolate content.

3. A *Brassica napus* plant line that produces seeds having a maximum total glucosinolate content of about 3.4 μmoles per g seed and a maximum 4-hydroxy-3-indolylmethyl glucosinolate content of about 1.9 μmoles per g seed, wherein said total glucosinolate content is obtained by genetic mutation.

* * * * *